US005738113A

United States Patent [19]
Connelly

[11] Patent Number: 5,738,113
[45] Date of Patent: Apr. 14, 1998

[54] CARIES TREATMENT METHOD WITH FLUORIDE

[75] Inventor: John Jude Connelly, Ottawa, Canada

[73] Assignee: Knowell Therapeutic Technologies, Inc., Ontario, Canada

[21] Appl. No.: 614,145

[22] Filed: Mar. 12, 1996

[51] Int. Cl.⁶ .................................................. A61B 19/00
[52] U.S. Cl. ..................... 128/898; 433/215; 433/217.1; 433/229
[58] Field of Search ............................ 424/401; 433/215, 433/216, 217.1, 229; 128/898

[56] References Cited

U.S. PATENT DOCUMENTS

| | | | |
|---|---|---|---|
| 4,692,407 | 9/1987 | Jordan et al. | 435/36 |
| 4,883,534 | 11/1989 | Sandham et al. | 106/35 |
| 5,476,647 | 12/1995 | Chow et al. | 424/52 |

FOREIGN PATENT DOCUMENTS

| | | |
|---|---|---|
| 1235986 | 5/1988 | Canada . |
| 2115853A1 | 8/1995 | Canada . |
| WO95/22308 | 8/1995 | WIPO . |

OTHER PUBLICATIONS

Caufield et al. "Effect of topically-applied solutions of iodine, sodium fluoride, or chlorhexidine on oral bacteria and caries in rats." J Dent Res 60(5):927–932, May 1981.

Carlos "The prevention of dental caries: ten years later." JADA 104: 193–197, Feb. 1982.

Keltjens et al. "Microbial aspects of preventive regimes in patients with overdentures." J Dent Res 66(10):1579–1582, Oct. 1987.

Duckworth et al. "Fluoride in saliva and plaque following use of fluoride-containing mouthwashes." J Dent Res 66(12):1730–34, Dec. 1987.

Bradshaw et al. "Preventionn of population shifts in oral microbial communities in vitro by low fluoride concentrations." J Dent Res 69(2):436–441, Feb. 1990.

Schaeken et al. "Effects of fluoride and chlorhexidine on the microflora of dental root surfaces and progression of root-surface caries." J Dent Res 70(2):150–153, Feb. 1991.

Sandham et al. "Clinical trial in adults of an antimicrobial varnish for reducing mutans streptococci." J Dent Res 70(11):1401–8, Nov. 1991.

Anderson et al. "Modern management of dental caries: the cutting edge in not the dental bur." JADA 124:37–44, Jun. 1993.

*Primary Examiner*—Vincent Millin
*Assistant Examiner*—Kelly O'Hara
*Attorney, Agent, or Firm*—Burns, Doane, Swecker & Mathis, L.L.P.

[57] ABSTRACT

A method for the control and reduction of dental caries is provided for individuals who are at risk of dental caries. The method comprising a first step of applying an antimicrobial treatment followed shortly thereafter by a second step of applying a fluoride treatment.

A method for the diagnosis, control and reduction of dental caries, the method comprising testing for *Streptococcus mutans* in an oral cavity of a patient and determining the patient's risk level for developing dental caries, to establish what treatment, if any, the patient requires in accordance with a set of treatment guidelines.

24 Claims, No Drawings

# 5,738,113

CARIES TREATMENT METHOD WITH FLUORIDE

FIELD OF THE INVENTION

The present invention relates to a method for the diagnosis and reduction of dental caries. More specifically, the method of the present invention relates to uses of a *Streptococcus mutans* monitoring test in association with fluoride and chlorhexidine. More particularly the present invention relates to an improvement in the control and reduction of dental caries by the use of fluoride in association with an antimicrobial agent such as chlorhexidine and a *Streptococcus mutans* monitoring test.

BACKGROUND OF THE INVENTION

Affordability, predictability and true prevention as the bases for dental treatments are increasingly the concerns of more and more dental patients. Increasingly, dentists are required to provide more cost-effective services for both the insured patient and the uninsured patient.

Effective medical management of dental caries is required particularly for those populations of patients that exhibit increased risk factors for caries. It is known that the presence of dental caries in certain patient subpopulations accounts for a substantial proportion of the dental caries seen in the population at large. In his article entitled, "The Medical Management of Dental Caries" (JADA, Vol. 125, January 1994, pp 31S to 39S), Edelstein quotes the U.S. Oral Health Coordinating Committee claim that 25% of U.S. children accounted for 75% of dental caries in 1986–1987. He also notes that caries among children world-wide is evident in many developing countries and much of Central Europe.

Another example of a population at risk of caries activity are older adults. Clinical needs for creation of new dental care treatments are emerging as the population ages. Effective dental care must meet the clinical needs of older patients who have root caries and limited salivary now (xerostomia).

The complexity inherent in the causative factors for developing dental caries coupled with the inertia of traditional dentistry methodologies, has delayed interest by the dental profession in preventive medical management of dental caries. As Edelstein points out in his paper (1994, supra), cariologists and epidemiologists rarely experience the dynamics and constraints of dental practice. They are, therefore, hampered in their efforts to translate their findings into clinical protocols. There remains a need for effective and cost effective treatment methods for dental caries.

U.S. Pat. No. 4,496,322 issued to Sandham and Balanyk discloses a varnish which may be applied to teeth which contains a dentally acceptable antimicrobial agent, such as chlorhexidine acetate, a benzoin gum, and an orally acceptable solvent. The composition, once applied to the teeth, is allowed to dry thereon and gives a transparent, translucent or tooth coloured film which is effectively invisible, but provides sustained release of the antimicrobial agent to an infection site over a period of a few days. To further improve the effect of the applied composition, the above inventors in their U.S. Pat. No. 4,883,534, describe the use of a sealing composition applied over the varnish. The sealing composition is preferably solvated polyurethane which upon evaporation of solvent is cured.

In Canadian Patent No. 1,235,986 which issued May 3, 1988 to Jordan and Marmel, there is disclosed a test kit and method for the determination of *Streptococcus mutans* in the oral cavity of a dental patient. The test is a semi-quantitative determination which is suitable for use by dentists and dental professionals in a non-laboratory environment. The test kit is sold commercially under the trade-mark CARIESCREEN SM by APO Diagnostics Inc. of Markham, Ontario, Canada. The test is an in vitro semi-quantitative dip-slide culture test for the detection of *Streptococcus mutans* in the oral cavity by use of a selective culture medium. The test uses a selective medium which, when used in conjunction with the diluent plus a dissolved bacitracin tablet, inhibits the growth of most salivary bacteria except for *Streptococcus mutans*. A carbon dioxide generating tablet is used to provide a carbon dioxide environment which enhances the growth of *Streptococcus mutans*.

International Patent Application PCT/CA95/00081, published on Aug. 24, 1995, in the name of Knowell Therapeutic Technologies Inc. teaches the combination of the two stage antimicrobial coating proposed by Sandham and Balanyk together with a *Streptococcus mutans* monitoring test, such as that provided commercially under the trade-mark CARIESCREEN SM. They teach that this combination may be used most effectively to not only monitor and reduce the levels of *Streptococcus mutans* bacteria, but also to determine the number and timing of two stage antimicrobial coating treatments necessary for a particular patient.

Medical and/or pharmaceutical interventions require minimal dental infrastructure and as such are desirable in markets of undeveloped countries and under-serviced poor communities.

It has now been found that an improvement on the methodology taught in International Patent Application PCT/CA95/00081 will further stabilize the oral cavity so that it is more resistant to the cariogenic effects of cariogenic bacteria such as *Streptococcus mutans* and Lactobacillus by the inclusion of fluoride. It has also now been recognized that the methods of the present invention, which are non-surgical medical interventions, will reduce the costs associated with restorative and prosthetic dental procedures. The cost of restorative dentistry can therefore be reduced for patients who are at medium or high risk of dental caries.

SUMMARY OF THE INVENTION

This invention provides an improved method and combination dental treatment for the medical management of dental caries, particularly in populations at increased risk of dental caries. The method and treatment combination of the present invention provide a medical or pharmaceutical model for dental treatment which significantly improves the health of the patient's teeth with beneficial cost efficiencies while minimizing the dental infrastructure surrounding patient treatment. The present invention therefore has the potential for significant cost savings in the treatment of dental caries as well as significant improvements in patient care and patient management.

According to an aspect of the present invention, a method for the control and reduction of dental caries is provided for individuals who are at risk of dental caries. The method comprises a first step of applying an antimicrobial treatment followed shortly thereafter by a second step applying a fluoride treatment.

According to another aspect of the present invention methods of diagnosis, control and reduction of dental caries are provided comprising testing for *Streptococcus mutans* in an oral cavity of a patient and determining the patient's risk level for developing denial caries, to establish what treatment, if any, the patient requires in accordance with the following guidelines:

a. objectively measuring the level of *Streptococcus mutans* in a patient's oral catty;
b. for a patient assessed at medium risk for *Streptococcus mutans* in the oral cavity, the following treatments are given to the patient:
   (i) one initial treatment with an antimicrobial agent in the first month of treatment and then one treatment with an antimicrobial agent at each recall visit thereafter; and
   (ii) daily fluoride treatments for a period of about sixty days after each antimicrobial treatment identified in step (b)(i);
c. for a patient assessed to be at high risk of *Streptococcus mutans* in the oral cavity, the following treatments are given to the patient;
   (i) at least two treatments with an antimicrobial agent in the first month of treatment and then one treatment with an antimicrobial agent at each recall visit thereafter; and
   (ii) daily fluoride treatments for a period of time after each antimicrobial treatment identified in step (c)(i);
d. for a patient assessed at lower risk for *Streptococcus mutans* in the oral cavity, the patient does not receive a treatment with an antimicrobial agent and the patient is given daily fluoride treatments for a period of time following the measurement of the *Streptococcus mutans* levels.

It is expected that the average patient will have a recall visit to the dentist either for prophylaxis or for cleaning about once every six months. Although for patients in the high risk group, recall visits may occur as early as three months after treatment. At recall visits objective measurement and assessment of patient risk for dental caries can be measured and evaluated.

An advantage of one aspect of the present invention is that the treatments of the present invention can be practiced, in part, at home thereby significantly reducing the costs associated with dental visits. At home practice could include. for example, tooth pastes containing an antimicrobial and/or a fluoride and also dental flosses which have been treated with an antimicrobial and/or a fluoride. In preferred embodiments the antimicrobial would be chlorhexidine. In other preferred embodiments the fluoride would be selected to maximize protection levels and optimize opportunities for remineralization while minimizing risks of dental staining. In all instances, the doses are kept well below thresholds based on body weight and other factors known to the metrical and dental professions.

According to a preferred embodiment of the present invention, the chlorhexidine treatment is applied by the dentist as a coating. The chlorhexidine continues to act on the teeth for several hours, and possibly days, after it has been applied by the dentist. This advantageously creates the necessary environment for fluoride optimization, in accordance with the present invention.

Other and further advantages and features of the invention will be apparent to those skilled in the art from the detailed description thereof.

DETAILED DESCRIPTION OF PREFERRED EMBODIMENTS

Studies of Canadian patients show that between 30% and 40% have *Streptococcus mutans* infections in their oral cavities at levels above 250.000 colony forming traits per milliliter (cfu/ml). The level of 250.000 cfu/ml is an internationally recognized standard of caries risk (see I. Zickert et al, "Effect of Caries Preventive Measures in Children Highly Infected with the Bacterium *Streptococcus mutans*, in J. Oral Biol., 1982. pp.861–868).

In Canada, the majority of Canadian patients are at low risk of dental caries. Typically, 10% of patients are high risk and 20% are medium risk as measured by the levels of *Streptococcus mutans* in their oral cavity. There are certain objective measures of *Streptococcus mutans* levels which are available to determine whether a patient is at high or medium risk of caries. Testing procedures are available in the market place. For example, one test kit is sold commercially under the trade-mark CARIESCREEN SM by APO Diagnostics Inc. of Markham, Ontario, Canada or the STRIP MUTANS test manufactured by Ivoclar-Vivadent. Categorisation of patients into low risk, medium risk and high risk is essential to provide the optimal frequency of dental treatments to prevent future dental caries. This is a significant factor as those at medium risk and high risk who are left untreated will be at greater risk of developing the disease. The testing can be performed by dentists.

In addition to the necessity of objectively measuring *Streptococcus mutans* levels in the oral cavity, it is necessary to be familiar with the dental and medical history of the patient, the oral hygiene habits of the patient, the age of the patient, and the type of medications the patient is taking (if any). It is known that the presence of *Streptococcus mutans* is essential for the development of dental caries. It is also known in the dental profession that certain risk factors operate in determining caries risk. These risk factors and their respective groupings are set out in Table 1 below.

TABLE 1

FACTORS IN DETERMINING CARIES RISK

| RISK FACTOR | HIGH RISK | MEDIUM RISK | LOW RISK |
|---|---|---|---|
| *Streptococcus mutans* (cfu/ml of saliva) | +500,000 | 250,000 to 500,000 | <250,000 |
| Decay Status | Recurrent, active, residual | episodic | dormant, none |
| Medication | xerostomia - related | not apparent | not apparent |
| Retention Sites | crown & bridge, orthodontic | moderate in number | few |
| Salivary Flow | Limited | Normal | Normal |
| Compliance to Treatment/Care | Poor | Average | Good |
| Cross-Infection Possibilities | Young Family | Young Family | |

While low risk is indicated as having less than about 250,000 cfu/ml *Streptococcus mutans*, one could distinguish further between a lower risk group having 100.000 to 250.000 cfu and a very low risk group at less than 100.000 cfu. Patients who could be at medium to high risk of dental caries are the patient group that will benefit from the combination treatment of the present invention, namely combining antimicrobial treatment with fluoride treatment as described in further detail herein. In particularly preferred embodiment the dental treatment protocol of the present invention is most beneficial in the group of patients at high risk with an oral concentration of *Streptococcus mutans* greater than 500,000 cfu.

Antimicrobial treatment is preferred to antibiotic treatment since the antimicrobial may be given for a long period of time without the risk of developing resistant strains as is the case with antibiotics.

Objective measurements of levels of *Streptococcus mutans* can be used as an indicator of an individual's likelihood of developing dental caries in the future as well as control of existing dental caries. Furthermore, it is recognized as an aspect of the present invention, that the change in the concentration of *Streptococcus mutans* in the oral cavity in response to a first treatment with an antimicrobial and a second treatment with a fluoride could be predictive of a patient's future risk of dental caries.

In the present invention, objective measures of caries risk are assessed by the dentist and usually measured by the concentration of *Streptococcus mutans* in the oral cavity. In other embodiments of the present invention other objective measures my be used together with the *Streptococcus mutans* measurement including, but not limited to, the number of existing fillings, age of the patient and other medication that the patient is taking.

The relationships between bacterial counts in the oral cavity and the development of dental decay and future prognosis in a patient are still being investigated. The treatment protocols of the present invention are advantageous in that they provide the dentist or dental treatment provider with a tool to control and reduce the incidence of dental caries. The treatment is particularly beneficial for reducing patient risk of dental caries in the population of patients with good nutritional habits and good habits of dental hygiene.

A patient in a high risk group could be treated and monitored with the methods of the present invention to see if their risk grouping drops to medium risk. Similarly those in the medium risk could be monitored to see if they move to a low risk group. The treatment guidelines for the new risk group would then apply. If a patient did not drop into a lower risk group then the dental treatment provider would know to continue with the current treatment for that risk group. This may also signal to the dentist that other factors which were not at first appreciated or realized may be at work. In the latter situation, the treatment methods of the present invention may act as an indictor of the overall oral health of the patient.

Each of the factors set out in Table 1 is assessed by the patient's dentist. In order to determine which patients are most likely to have high *Streptococcus mutans* levels in their oral cavities, the dentist uses an assessment test similar to CARIESCREEN™ to measure the concentration of *Streptococcus mutans* in the oral cavity. The dentist may also use their clinical judgment to assess the patient's overall condition. Clinical factors used when deciding whether a patient is at medium to high risk of caries include:

patients with recurrent or residual decay, as shown by their treatment history;

patients who are about to receive orthodontic care (as it is known that orthodontic appliances and/or brackets are natural sites for colonization of *Streptococcus mutans*;

patients with crown and bridge restorations; patients with limited salivary flow (xerostomia) for example due to systemic medication (e.g. anti-hypertensives, anti-depressants, tranquilizers, antihistamines, and other drugs known to reduce saliva flow), systemic disease (e.g. Sjogren's Syndrome, scleroderma, lupus, rheumatoid arthritis), or with neurological conditions (e.g. Parkinson's Disease);

new patients exhibiting poor oral hygiene, poor dental knowledge and/or poor compliance;

patients under periodontal care with exposed root surfaces young mothers who have children between the ages of 2 and 3 (without treatment the mothers could readily transmit the infection to their children since children are not colonized by *Streptococcus mutans* at birth, only later by cross-infection)

patients at peak periods for decay—in their early teens, 20's and over 55 years of age.

Patients likely to be at medium or high risk of developing caries are tested using a test that measures the levels of *Streptococcus mutans* in the oral cavity of the patient. In a preferred embodiment of the present invention, the CARIESCREEN™ brand of test is used to detect *Streptococcus mutans*. This is a five minute test and complete instructions are available with the test kit purchase. Furthermore the test is described in detail in Canadian Patent No. 1,235,986. Generally, the test may be described in the following manner The CARIESCREEN SM test kit generally comprises the following components:

1. a sealed container for an antiseptic solid substrate, which substrate has at least one surface coated with a selected solid medium to reduce the growth of *Streptococcus mutans* and a predetermined amount of saccharide compound;

2. a second sealed container for a buffered saline solution into which a test sample is deposited for determining *Streptococcus mutans* level;

3. a solid bacitracin composition in an amount and concentration, which in combination with the quantity of saccharide is not sufficient to preclude growth of *Streptococcus mutans*, but is sufficient to prevent growth of substantial amounts of any interfering microorganism;

4. a carbon dioxide generating composition for providing a carbon dioxide atmosphere for incubation of the solid substrate;

5. means are included to examine the surface of the incubated solid substrate for the colony density of *Streptococcus mutans*;

6. means are provided to prepare the colony density of the tested *Streptococcus mutans* with a comparison standard in order to determine in a semi-quantitative manner colony density of the *Streptococcus mutans* of the test sample; and 7. an incubator container for incubation of the solid substrate surface after contact by the buffered saline solution containing the bacitracin composition and the test sample. The carbon dioxide generating composition is placed in this incubation container and after the solid substrate has been allowed to remain in the incubator for a period of time, it is then examined and compared to a standard to determine the colony density of the *Streptococcus mutans* in the test sample.

Other types of *Streptococcus mutans* bacteria test kits and testing methods are available commercially and one skilled in the art would know that may be used in the methods of the present invention.

The results from the *Streptococcus mutans* test will indicate the concentration of *Streptococcus mutans* in the saliva as measured in colony forming units per milliliter of saliva (cfu/ml). If a patient is confirmed by the *Streptococcus mutans* test results to fall within the medium to high risk groups then the patient is a good candidate for the treatment methodology of the present invention. As noted in Table 1 above, the high risk group is characterized as having levels of *Streptococcus mutans* above about 500,000 cfu/ml. The medium risk group is characterized as having between about 250,000 cfu/ml and about 500,000 cfu/ml. Even if the *Streptococcus mutans* results are less than about 250,000 cfu/ml the patient may still benefit from the treatment method of the present invention, particularly if they have one or more of the other risk factors identified in Table 1.

Before proceeding with the next step of antimicrobial treatment, the patient's dentist may first wish to ensure that full dentition has been restored and is without decay, including all open caries lesions; however, a surprising advantage of the present invention is that if the patient and dentist follow the protocols of the methods of the present invention strictly, incipient decay need not be treated. It is an advantage of the present invention that one can proceed with the combination treatment protocol of the present invention to effectively treat the patient in some instances without first achieving full dentition without decay. This is clearly a preferred approach since it reduces the need for fillings or other treatments which can actually increase the risk of *Streptococcus mutans* growing in the oral cavity. It is recommended that the patient be monitored with an annual radiograph and biannual clinical examinations to ensure strict compliance has occurred.

The present invention teaches that the combining of fluoride treatments, with antimicrobial treatments coupled with routine and regular dental hygiene practices can serve to be indicative of the patient's oral hygiene status as well as control and reduce the incidence at dental caries which is one of the most commonly occurring diseases in humans. It is also recognized that the methods of the present invention may have veterinary applicability. For example, in addition to the combination of the CARIESCREEN™ testing and CHLORZOIN™ (as taught in the International Patent Application PCT/CA95/00081 described above), provides distinct advantages in the success of the patient's long term benefits of caries reductions and prevention. One further advantage of the methods of the present invention is the significant cost benefits to the patient and/or to the insurer. Therefore, the proposed caries treatment method with fluoride demonstrates benefits in cost and in effectiveness at reducing the incidence of caries.

In addition, the method permits the early treatment and reduction of *Streptococcus mutans* in the oral cavity to levels that can be maintained to reduce significantly the need for future costly restorative work. The treatment methods of the present invention are grounded on conducting chlorhexidine treatment preferably in the dental office (to ensure compliance and proper drug administration), and subsequently providing fluoride home care products to the patient. The dentist will explain the products to the patient during the patient visits. This will help to ensure patient understanding and use thereby optimizing patient compliance. The treatment regimens of the present invention isolate patients at risk of disease and then doses therapeutically according to risk.

Antimicrobial and fluoride are complementary in that they affect the opposite phases of the demineralization-remineralization cycle of the tooth surface. Chlorhexidine (for example as sold under the brand name CHLORZOIN™) controls the demineralization cycle of the tooth surface, by directly controlling the plaque and the plaque's production of the acids. Ultimately this can influence the overall pH of the oral cavity or regions of the oral cavity. Fluorides (for example, the fluoride product sold under the brand name FLUORZOIN™), on the other hand, encourages remineralization. The use of the two together achieves an effect that is not achieved by each alone as the antimicrobial has the effect of preparing the environment so it can optimize the benefits of the fluoride treatment.

The significant advantage of one of the preferred embodiments of the method of the present invention is that the antimicrobial treatment is applied by the dentist and when incorporated into the method of the present invention, significantly increases patient compliance and effectiveness of the treatment protocols.

It is known that both chlorhexidine and fluoride treatments act to inhibit bacterial acid production (C. Emilson, (1994). J. Dent. Res., v.73, March 1994, pp. 682–691). Fluoride's ability to reduce the solubility of enamel is typically not compromised chemically by the presence of chlorhexidine and as noted above the two chemicals work at different phases of the demineralization-remineralization cycle.

In a preferred embodiment of the present invention chlorhexidine is applied by the dentist in a relatively high concentration (as compared to the concentration in oral rinses or gels). In a preferred embodiment the concentration ranges from about 10% to about 20%. In a more preferred embodiment the concentration is about 10%, as applied by the dentist. The chlorhexidine continues to be released into the oral cavity for about 8 hours and sometimes longer. Surprisingly, this sustained release enhances the antimicrobial effect of the chlorhexidine without causing the common adverse effects of staining, loss of taste acuity and poor patient compliance. It may also be the case that the chlorhexidine is absorbed into the enamel of the tooth where it continues to have an effect. The preferred embodiments of the present invention integrate fluoride treatments into this process to obtain improved protection against dental caries and/or improved treatment of dental caries.

In a preferred embodiment for a patient at high risk, at least two initial treatments with an antimicrobial agent are provided in the first month of treatment. Typically the treatments would be spaced about 2 weeks apart. In another preferred embodiment, the high risk patient would receive 3 initial treatments with an antimicrobial agent, preferably chlorhexidine, within the first month of treatment. The patient would then be given one antimicrobial treatment at each recall visit thereafter. After receiving the antimicrobial treatment then daily fluoride treatments would follow for the period of time between the initial treatments and then for a period of about 90 days to about 120 days after the last of the initial antimicrobial treatments.

For the high risk patient, the antimicrobial would be re-applied at the patient's next recall visit in accordance with the test results for *Streptococcus mutans* levels measured and other objective measures as would be known to the dentist. At the recall visit, around 4 to 6 months for a high risk patient, the patient would receive another antimicrobial treatment followed by about 120 daily fluoride treatments.

For the medium risk patient, in a preferred embodiment the initial treatment would consist of one antimicrobial agent, preferably chlorhexidine, and about 60 days of daily fluoride treatments following thereafter. At recall visits, usually 6 months apart, the medium risk patient would be re-tested for *Streptococcus mutans* and treated according to the guidelines of the present invention based on the *Streptococcus mutans* test results and other objective measures.

Patients in the lower risk groups of about 100,000 to about 250,000 cfu and less than about 100,000 cfu do not require the antimicrobial treatment unless other measures would suggest that the patient's risk is higher than the cfu count alone would suggest. Patients in the about 100,000 to 250,000 range may still benefit from a course of daily fluoride treatments for about 60 days.

The mechanism of action of fluoride is not completely understood, despite a large body of epidemiological data (R. Duckworth and D. Stewart, (1990) J. Dent. Res., vol. 69, pp.436 to 441). Many different fluoride regimens (dosing, concentrations, different carriers and types of fluoride) have been effective against caries; but the most critical factor appears to be proper patient use on a sustained basis (J. Brodeur et al., (1990), CDA Journal, v.56 at pp. 53–56). To be effective in remineralization, the fluoride ion has to be at the site of the developing lesion (Duckworth, op. cit.; R. Duckworth et al, (1987), J. Dent. Res., v. 66 at pp. 170–174). There are reservoirs of fluoride in the upper anterior vestibule which retain this ingredient and make it available over periods of time to the rest of the mouth (L. Petersson, Caries Res., v.27, 1993, pp. 35–42). Fluoride challenges alone, however, have not controlled the acid challenge and have not therefore been historically delivered as part of an overall treatment plan. The recognition in the present invention of the benefits of first treating with an antimicrobial now makes the use of fluoride in an overall treatment plan much more attractive and effective for the patient at risk of dental caries.

In accordance with the present invention, Patients tested and found to be at risk of caries are given an antimicrobial treatment. Table 2, below, details a preferred dosing regimen for the antimicrobial treatment.

TABLE 2

PREFERRED ANTIMICROBIAL DOSING REGIMEN

| PATIENT RISK GROUP | BASELINE ANTIMICROBIAL TREATMENTS | RECALL ANTIMICROBIAL TREATMENTS |
| --- | --- | --- |
| HIGH RISK | 3 in first month | 1 per recall |
| MEDIUM RISK | 1 | 1 per recall |
| LOW RISK | 0 | 0 |

In one preferred embodiment of the present invention, the antimicrobial agent is selected from the group consisting of chlorhexidine and/or salts of chlorhexidine. In another preferred embodiment of the present invention, the antimicrobial agent is an orally and biologically acceptable source of chlorhexidine. In another preferred embodiment of the present invention, the chlorhexidine is a topically, biologically acceptable preparation.

In another preferred embodiment of the present invention the antimicrobial agent is selected from the group of chlorhexidine salts consisting of chlorhexidine acetate, chlorhexidine hydrochloride and chlorhexidine gluconate. In yet another preferred embodiment of the present invention the antimicrobial agent is chlorhexidine acetate.

In another preferred embodiment of the present invention, patients tested and found to be at risk of caries are treated with CHLORZOIN™, and dosed according to risk levels. High risk patients are treated more aggressively with more dosing and a longer treatment period than medium risk patients. Examples of the appropriate dosing regimens are found in Table 2, above.

The incorporation of the fluoride treatment is the next step in the in the treatment method for the reduction of caries of the present invention. High and medium risk patients follow difficult regimens of fluoride treatment at home, after their professional care with the antimicrobial treatment. In addition to the surprising enhanced benefits of combining the fluoride and chlorhexidine together into a dental protocol, the fact that the fluoride component of the treatment regimens may be incorporated into patient home care is a significant advantage because of increased compliance and reduced overall costs.

Preferred fluoride treatment regimens of the present invention incorporate both fluoride gel (stannous fluoride) and fluoride rinse (sodium fluoride) treatment regimens. In a preferred embodiment, the product FLUORZOIN™ is used as the source of fluoride for the fluoride regimen. Table 3, below, outlines preferred embodiments for a course of treatment incorporating the FLUORZOIN™ home care pack. The home care pack contains two 227 mL bottles of FLUORZOIN™ oral rinse containing 0.023% fluoride ion from 0.05% sodium fluoride and one 60 mL squeeze boric of FLUORZOIN™ gel containing 0.4% stannous fluoride and one new toothbrush. One home care pack should last for 60 days of usage.

Other suitable concentrations and combinations of fluoride would be understood to be operable by a person skilled in the art who has had the benefit of the present disclosure. Factors to be considered when selecting an appropriate fluoride source, type and dosage are patient compliance, taste, potential for staining of teeth as well therapeutically acceptable thresholds for the person's age, weight and medical status.

TABLE 3

FLUORZOIN ™ HOME CARE TREATMENT REGIMEN AFTER ANTIMICROBIAL TREATMENT

| PATIENT RISK GROUP | FLUORZOIN ™ Home Care Pack (2 × 227 ml NaF rinse + 1 × 60 ml SF gel + toothbrush - sufficient for 60 days) |
| --- | --- |
| HIGH RISK | 120 days Fluoride Home Care |
| MEDIUM RISK | 60 days Fluoride Home Care |
| LOWER RISK (between 100,000 and 250,000 cfu/ml of *Streptococcus mutans*) | none required |

Generally no fluoride home care treatment is necessary in the patient at low risk; however, sixty days of fluoride treatment may be advantageous if other risk factors are present in the patient which would predispose the patient to *Streptococcus mutans* growth in their oral cavity.

Microbiological studies of CHLORZOIN™ have shown that high risk patients require aggressive dosing to suppress the *Streptococcus mutans* for normal recall periods (Sandham, J. (1991), J. Dent. Res., vol. 70 at pp. 1401–1408; Sanaham, J. (1992), J. Dent. Res., vol. 71, at pp. 32–35). Medium risk patients require less dosing and a shorter treatment period. An optimal dosing of fluoride in the present invention is to attain and maintain a high frequency, low fluoride concentration in the oral fluids. For example, fluoride should preferably be used at bed time after normal brushing of the teeth because the salivary secretion rate and welling of oral fluid are minimal at that time.

Generally, the use of FLUORZOIN™ oral rinse or in combination with FLUORZOIN™ gel in combination with twice daily use of fluoride dentifrice can achieve fluoride concentrations in the optimal range for several hours a day. This is particularly mac of the mouth rinse and gel because these are not rinsed from the mouth after use. In high risk adults, higher salivary fluoride levels, associated with greater caries protection, can also be achieved during the daytime if they arc able to refrain from rinsing, or rinse minimally, after the use of fluoride dentifrice.

A distinct benefit of using a fluoride gel such as the FLUORZOIN™ gel is that it could help to maintain *Streptococcus mutans* at low levels after treatment with a chlorhexidine product such as CHLORZOIN™.

The safety and efficacy of the dosing regimen described herein is described as follows. CHLORZOIN™ has been approved by the Health Protection Branch of the Canadian Government after a full assessment of toxicity at dosing levels greater than suggested. CHLORZOIN™ contains chlorhexidine acetate which has an LD$_{50}$ of 2 liters; per single treatment of CHLORZOIN™ a patient would receive about 0.05 mL of chlorhexidine.

Following correct rinsing or gel application only a small proportion of fluoride is retained or swallowed. It has been suggested that only about 15% of an oral rinse is ingested (see L. Petersson, (1993) Caries Res., vol. 27, at pp 35 to 42). Therefore the inadvertent, intentional or accidental swallowing of an entire volume (10 mL) of FLUORZOIN™ rinse or an entire portion (1 g) of FLUORZOIN™ gel would still result in values generally far below the 5 mg per kg body weight generally accepted to be a health hazard in humans.

While fluoride oral rinsing (and home gel use) are safe from the medical standpoint, they are not recommended for children under 7 years of age because there is a significant risk that the entire dose could be consistently swallowed, thereby increasing the risk of enamel fluorosis.

For children under the age of seven the treatment of the present application is modified to eliminate the home use of FLUORZOIN™ oral rinse or FLUORZOIN™ oral gel because of their intake of fluoride from other sources including fluoride dentifrice.

The fluoride in the method of the present application is significantly less per treatment than the fluoride gels typically used in dental offices. The 1.23% APF gels used in professional in-office fluoride treatments expose the patient to considerably higher doses of fluoride, averaging 60 mg per treatment, than the method detailed herein. In addition, the application of CHLORZOIN™ after the topical foam treatment spreads the ingestion of fluoride over a much longer period of time, as noted from studies of fluoride varnish (J. Ekstrand et al, (1980), Caries Res., vol. 14 at pp. 185–189).

"Further details of the preferred embodiments of the invention are illustrated in the following Examples which are understood to be non-limiting with respect to the appended claims."

EXAMPLES

Table 4, below, outlines preferred treatment methodologies for three risk groups by way of examples of the present invention. In these examples, the preferred fluoride treatment is provided by the patient at home by way of a combination of FLUORZOIN™ gel and rinse. The fluoride gel is in a preferred concentration of 0.4% stannous fluoride (SF). The fluoride rinse is in a preferred concentration of 0.05% sodium fluoride (NaF).

In Table 4, below, examples of preferred treatment methodologies for the three risk groups are detailed.

TABLE 4

| TREATMENT GROUP | MICROBIOLOGICAL TESTING | ANTIMICROBIAL TREATMENTS IN THE DENTAL OFFICE | FLUORIDE TREATMENTS AT HOME BY THE PATIENT |
|---|---|---|---|
| HIGH RISK (above 500,000 cfu) | baseline and annually thereafter | 3 treatments in first month and once every 6 months thereafter | FLUORZOIN ™ gel (0.4% SF) before bed + FLUORZOIN ™ rinse (0.05% NaF) after breakfast each day for 120 days after antimicrobial treatment |
| MEDIUM RISK (250,000 to 500,000 cfu) | baseline and annually thereafter | 1 initial treatment in first month and at every 6 month recall visit thereafter | same FLUORZOIN ™ protocol as above for 60 days after antimicrobial treatment |
| LOW RISK (less than 250,000 cfu) | baseline and annually thereafter | no treatment, routine prophylactic recall visits to dentist every 6 months | same FLUORZOIN ™ protocol as above 60 days after prophylactic if over 100,000 cfu/ml Streptococcus mutans, particularly if other risk |

Although preferred embodiments of the invention have been described herein, it will be understood by those skilled in the art that variations, modifications, and equivalents may be made thereto without departing from the spirit of the invention or the scope of the appended claims.

I claim:

1. A method for the diagnosis, control and reduction of dental caries, the method comprising testing for *Streptococcus mutans* in an oral cavity of a patient and determining the patient's risk level for developing dental caries, to establish what treatment, if any, the patient requires in accordance with the following guidelines:
   a. objectively measuring the level of *Streptococcus mutans* in a patient's oral cavity;
   b. for a patient assessed at medium risk for *Streptococcus mutans* in the oral cavity, the following treatments are given to the patient:
      (i) one initial treatment with an antimicrobial agent in the first month of treatment and then one treatment with an antimicrobial agent at each 6 month recall visit thereafter; and
      (ii) daily fluoride treatments for a period of sixty days after each antimicrobial treatment identified in step (b)(i);
   c. for a patient assessed to be at high risk of *Streptococcus mutans* in the oral cavity, the following treatments are given to the patient:
      (i) at least two treatments with an antimicrobial agent in the first month of treatment and then one treatment with the antimicrobial agent at each 4–6 month recall visit thereafter; and
      (ii) daily fluoride treatments for a period of up to 120 days after each antimicrobial treatment identified in step (c)(i);
   d. for a patient assessed at lower risk for *Streptococcus mutans* in the oral cavity, the patient does not receive a treatment with an antimicrobial agent and the patient is given daily fluoride treatments for a period of 60 days following the measurement of the *Streptococcus mutans* levels.

2. The method as claimed in claim 1 wherein the treatment with an antimicrobial agent is given at the dentist's office and the fluoride treatment is applied by the patient at home.

3. The method as claimed in claim 1 wherein the antimicrobial agent is selected from the group consisting of chlorhexidine and salts of chlorhexidine.

4. The method as claimed in claim 3 wherein the antimicrobial agent is an orally and biologically acceptable source of chlorhexidine.

5. The method as claimed in claim 3 wherein the antimicrobial agent is a topically and biologically acceptable source of chlorhexidine.

6. The method as claimed in claim 3 wherein the antimicrobial agent is selected from the group of chlorhexidine salts consisting of chlorhexidine acetate, chlorhexidine hydrochloride and chlorhexidine gluconate.

7. The method as claimed in claim 6 wherein the antimicrobial agent is chlorhexidine acetate.

8. The method as claimed in claim 1 wherein the fluoride treatment is a combination of a fluoride in the form of a gel, and a fluoride in the form of a mouth wash rinse.

9. The method as claimed in claim 8 wherein the fluoride gel is selected from the group consisting of stannous fluoride gel alone, sodium fluoride gel alone and a mixture of stannous fluoride gel and sodium fluoride gel, in a biologically acceptable concentration.

10. The method as claimed in claim 1 wherein the antimicrobial treatment is CHLORZOIN™ and the fluoride treatment is FLUORZOIN™.

11. The method as claimed in claim 1 wherein the patient in step (b) has levels of *Streptococcus mutans* ranging from about 250,000 colony forming units per milliliter (cfu/ml) to about 500,000 cfu/ml of saliva;

the patient in step (c) has levels of *Streptococcus mutans* in the oral cavity in excess of about 500,000 cfu/ml of saliva; and the patient in step (d) has levels of *Streptococcus mutans* in the oral cavity ranging from about 100,000 cfu/ml to about 250,000 cfu/ml of saliva.

12. A method for the diagnosis, control and reduction of dental caries, the method comprising testing for *Streptococcus mutans* in an oral cavity of a patient and determining the patient's risk level for developing dental caries, to establish what treatment, if any, the patient requires in accordance with the following guidelines:

a. objectively measuring the level of *Streptococcus mutans* in a patient's oral cavity;

b. for a patient assessed at medium risk for *Streptococcus mutans* in the oral cavity, the following treatments are given to the patient:
   (i) one initial treatment with an antimicrobial agent in the first month of treatment and then one treatment with an antimicrobial agent at each 6 month recall visit thereafter; and
   (ii) daily fluoride treatments for a period of about sixty days after each antimicrobial treatment identified in step (b)(i);

c. for a patient assessed to be at high risk of *Streptococcus mutans* in the oral cavity, the following treatments are given to the patient:
   (i) at least two treatments with an antimicrobial agent in the first month of treatment and then one treatment with the antimicrobial agent at each 4–6 month recall visit thereafter; and
   (ii) daily fluoride treatments for a period of up to 120 days after each antimicrobial treatment identified in step (c)(i);

d. for a patient assessed at lower risk for *Streptococcus mutans* in the oral cavity, the patient does not receive a treatment with an antimicrobial agent and the patient is given daily fluoride treatments for a period of 60 days following the measurement of the *Streptococcus mutans* levels.

13. The method as claimed in claim 12 wherein the treatment with an antimicrobial agent is given at the dentist's office and the fluoride treatment is applied by the patient at home.

14. The method as claim in claim 12 wherein the antimicrobial agent is selected from the group consisting of chlorhexidine and salts of chlorhexidine.

15. The method as claimed in claim 14 wherein the antimicrobial agent is an orally and biologically acceptable source of chlorhexidine.

16. The method as claimed in claim 14 wherein the antimicrobial agent is a topically and biologically acceptable source of chlorhexidine.

17. The method as claimed in claim 14 wherein the antimicrobial agent is selected from the group of chlorhexidine salts consisting of chlorhexidine acetate, chlorhexidine hydrochloride and chlorhexidine gluconate.

18. The method as claimed in claim 17 wherein the antimicrobial agent is chlorhexidine acetate.

19. The method as claimed in claim 12 wherein the fluoride treatment is a combination of a fluoride in the form of a gel, and a fluoride in the form of a mouth wash rinse.

20. The method as claimed in claim 19 wherein the fluoride gel is selected from the group consisting of stannous fluoride gel alone, sodium fluoride gel alone and a mixture of stannous fluoride gel and sodium fluoride gel, in a biologically acceptable concentration.

21. The method as claimed in claim 12 wherein the antimicrobial treatment is CHLORZOIN™ and the fluoride treatment is FLUORZOIN™.

22. The method as claimed in claim 12 wherein the patient in step (b), has levels of *Streptococcus mutans* ranging from about 250,000 colony forming units per milliliter (cfu/ml) to about 500,000 cfu/ml of saliva;

the patient in step (c) has levels of *Streptococcus mutans* in the oral cavity in excess of about 500,000 cfu/ml of saliva; and the patient in step (d) has levels of *Streptococcus mutans* in the oral cavity ranging from about 100,000 cfu/ml to about 250,000 cfu/ml of saliva.

23. The method as claimed in claim 11 wherein the fluoride treatment is applied each day for about 60 days after antimicrobial treatments for the patient in step (b);

the fluoride treatment is applied each day between antimicrobial treatments up to a maximum of about 120 days for the patient in step (c); and wherein the fluoride treatment is applied each day for a period of about 50 days for the patient in step (d).

24. The method as claimed in claim 22 wherein the fluoride treatment is applied each day for 60 days after antimicrobial treatments for the patient in step (b);

the fluoride treatment is applied each day between antimicrobial treatments up to a maximum of 120 days for the patient in step (c); and wherein the fluoride treatment is applied each day for a period of 60 days for the patient in step (d).

* * * * *